(12) United States Patent
O'Connor-Smith

(10) Patent No.: US 9,192,188 B2
(45) Date of Patent: Nov. 24, 2015

(54) NUTRITIONAL SUPPLEMENT

(71) Applicant: Delphine Agatha O'Connor-Smith, Saint Catherine (JM)

(72) Inventor: Delphine Agatha O'Connor-Smith, Saint Catherine (JM)

( * ) Notice: Subject to any disclaimer, the term of this patent is extended or adjusted under 35 U.S.C. 154(b) by 0 days.

(21) Appl. No.: 13/796,387

(22) Filed: Mar. 12, 2013

(65) Prior Publication Data

US 2014/0271947 A1 Sep. 18, 2014

(51) Int. Cl.
| | |
|---|---|
| A61K 36/45 | (2006.01) |
| A61K 36/886 | (2006.01) |
| A61K 36/42 | (2006.01) |
| A61K 36/185 | (2006.01) |
| A23L 2/02 | (2006.01) |
| A61K 36/21 | (2006.01) |
| A61K 36/23 | (2006.01) |
| A61K 36/752 | (2006.01) |

(52) U.S. Cl.
CPC . *A23L 2/02* (2013.01); *A61K 36/21* (2013.01); *A61K 36/23* (2013.01); *A61K 36/42* (2013.01); *A61K 36/45* (2013.01); *A61K 36/752* (2013.01); *A61K 36/886* (2013.01)

(58) Field of Classification Search
None
See application file for complete search history.

(56) References Cited

U.S. PATENT DOCUMENTS

| 6,133,318 A * | 10/2000 | Hart | 514/574 |
|---|---|---|---|
| 7,025,996 B1 | 4/2006 | Miladinov et al. | |
| 2001/0012525 A1 * | 8/2001 | Mann | 424/727 |
| 2006/0286188 A1 * | 12/2006 | Mower et al. | 424/777 |
| 2008/0131561 A1 * | 6/2008 | Patanawongyuneyong | 426/72 |

FOREIGN PATENT DOCUMENTS

| CN | 101147572 A | * | 3/2008 |
|---|---|---|---|
| CN | 102429288 A | | 5/2012 |
| CN | 102697116 A | | 10/2012 |
| CN | 102697118 A | | 10/2012 |
| DE | 20214195 U1 | * | 3/2004 |
| JM | 18/1/4616 | | 4/2007 |
| WO | 2009013395 A | | 1/2009 |
| WO | 2012005998 A | | 1/2012 |

OTHER PUBLICATIONS

DW2008-H54842, Jun. 2008, Derwent, Padana et al.*
Search Report, UK Application GB1310298.3, Dec. 9, 2013.
Spirit of Health Juice & Blended Drinks, http://www.spiritofhealthkc.com/portfolio/healthy-juice-drinks/, circa May 2013.

* cited by examiner

Primary Examiner — Chris R Tate
Assistant Examiner — Randall Winston
(74) Attorney, Agent, or Firm — Mark D. Perdue

(57) ABSTRACT

A dietary supplement and method of supplementation comprises a vegetable component consisting essentially of juices extracted from two parts by weight fresh, unpeeled carrots; one part by weight fresh, unpeeled beet root; one part by weight of fresh, unpeeled cucumber; and a selected quantity of *aloe vera* juice. A cleansing component includes at least one of the following: about 2 fluid ounces (59.1 ml) of lemon juice; about 1.5-2 fluid ounces (44.3 to 59.1 ml) of lime juice; about 1 fluid ounce (29.6 ml) of *aloe vera* juice; and about 4-6 fluid ounces (118.3 to 177.4 ml) of cranberry juice. The vegetable component is ingested orally twice daily and the cleansing component is ingested orally once daily.

12 Claims, No Drawings

NUTRITIONAL SUPPLEMENT

TECHNICAL FIELD

The present invention is a detailed and nutritional preparation of natural juice extracts designed to promote general health, particularly in those suffering from maladies such as arthritis and cancer.

BACKGROUND OF THE INVENTION

Cancer is a leading cause of death in some parts of the world which is perhaps due mainly to the fact that there is no official medical cure for the disease. While there are a number of cancer treatments such as radiation therapy, chemotherapy, immunotherapy and various forms of surgical procedures; many of these treatments can prove quite painful and rigorous on the person undergoing treatment.

Arthritis, of all varieties, is a painful and debilitating disease that, like cancer, has no known cure. Although it is typically not deadly like cancer, progression of the disease can cause significant pain and disability for sufferers. Also, treatments for rheumatoid arthritis, namely biologics and immunotherapy, share the rigors of similar treatments for cancer, and NSAID medications for pain and inflammation can have serious gastric side effects.

Due to the deadly nature of the disease of cancer and the pain inflicted by both cancer and arthritis, and the mixed results of some of the standard methods of treatment, it has been necessary to devise a supportive treatment that is simple, effective and would increase the chances of recovery of cancer and arthritis patients and contributes to the general health of those not afflicted. In more recent times, it has been discovered that a good number of life threatening diseases are directly linked to poor nutritional practices and that many fruits and vegetables have nutrients that are beneficial and may even prevent and/or stop the spread of cancer and arthritis.

Yet the random consumption or use of fruits and vegetables, in and of itself, does not treat or cure any disease. Not all fruits and vegetables are equal in their ability to treat cancer or arthritis, and as such the selective use of such fruits, vegetables and other natural products as used in the invention is necessary to effectively support health, particularly of those suffering from cancer or arthritis.

Given the excessive stress that a cancer patient goes through, the aforementioned methods of cancer treatment, such as radiation therapy, chemotherapy and immunotherapy, do not always provide the necessary nutrition and full therapy to help the body completely heal. As such the present invention is devised to supplement the existing methods and complete the treatment.

Similarly, the arthritis patient can benefit from nutritional support, both to reduce the inflammation characteristic of the disease and to minimize or alleviate the side effects and symptoms of certain treatments or therapies.

General use of such nutrients and other therapy can be insufficient and as such a specific formulation and regime, as embodied in the present invention, have been devised to effectively combat the symptoms of these deadly and painful diseases.

Prior art consists of raw food treatments for cancer such as the Brandt Grape treatment which involves the use of grape and grape juice, and books have been written on how raw or uncooked foods interact with diseases such as cancer. While many cancer diets are essentially a modification of a raw food diet, each cancer treatment diet or formula has its own unique attributes. Thus while the present invention contains some of the key ingredients found in some vegetable diets or therapies such as carrots or beets, it also has its own specific formulation and preparation techniques to maximize its effectiveness and which distinguishes it from any prior art.

Further some of the existing raw juice therapies rely on the use of one to two quarts of carrot juice daily. Such a high quantity of carrot juice would be highly laxative and result in constant discomfort to the patient. As a result of experiencing such discomfort, the patient may quickly abandon the therapy once his or her condition improves, which would only counteract the effects of the therapy. As the present invention does not have such a discomforting effect, the likelihood of a patient abandoning same is significantly reduced. Further, if the patient is a diabetic, the large quantities of simple sugars found in the quarts of carrot juice may pose a significant risk to the patient. The present invention does not pose such a risk.

The present invention's specific use of *aloe vera* in combination with the other stated ingredients in its vegetable therapy also distinguishes it from prior art.

U.S. Pat. No. 7,025,996 addresses a dietary supplement which is formulated for medical patients undergoing a chemotherapy treatment regimen. The present invention is distinguished from the said US patent as this invention does not solely involve providing a dietary supplement for cancer patients undergoing a chemotherapy treatment regime. Unlike the cited US patent, the invention is comprised solely of natural ingredients versus some of the chemically based-ingredients of the US patent.

SUMMARY OF THE INVENTION

This invention aims to promote general health and specifically that of cancer and arthritis patients by:
1. Providing a dietary and nutritional therapy that is specifically formulated to meet the nutritional needs of patients undergoing a cancer or arthritis treatment, by providing a complete or near complete supply of nutrients to such patients.
2. Providing a three-pronged therapy that, in particular, hinges on a selective and specific cleansing formulation that carefully balances the use of fruits, vegetables and the nutrients found within same that builds the immunity systems and contributes to cellular health.
3. Providing a treatment for imparting strength, energy, tissue healing and repair, growth and development, to all persons, and in particular treatment tolerance to a cancer patient undergoing a cancer treatment regime, such as radiation treatment, in a form that is readily available, easily digestable and nutritionally complete.
4. Providing a treatment that produces no known side effects.
5. Providing a cost-effective means of benefiting from the above-mentioned uses.

These and other objects of the present invention are achieved by a dietary supplement and method of supplementation comprising a vegetable component consisting essentially of juices extracted from two parts by weight fresh, unpeeled carrots; one part by weight fresh, unpeeled beet root; one part by weight of fresh, unpeeled cucumber; and a selected quantity of *aloe vera* juice. A cleansing component includes at least one of the following: about 2 fluid ounces (59.1 ml) of lemon juice; about 1.5-2 fluid ounces (44.4 to 59.1 ml) of lime juice; about 1 fluid ounce (29.6 ml) of *aloe vera* juice; and about 4-6 fluid ounces (118.3 to 177.4 ml) of cranberry juice. The vegetable component is ingested orally twice daily and the cleansing component is ingested orally once daily.

According to a preferred embodiment of the invention, each part of the vegetable component is about 4-5 ounces by weight (113.4 to 141.8 g); and the selected quantity of *aloe vera* juice is 1 teaspoon (5 to 10 ml).

According to a preferred embodiment of the invention, the vegetable component is about 6 to 8 fluid ounces (177.4 to 236.6 ml).

According to a preferred embodiment of the invention, the *aloe vera* juice comprises about 225 grams washed and cut, untrimmed, fresh, green *aloe vera* plant with intact skin, the *aloe vera* blended with about 500 ml. of water and strained.

Other objects, features and advantages of the present invention will become apparent with reference to the detailed description, which follows.

DETAILED DESCRIPTION OF THE INVENTION

Patients diagnosed with cancer usually undergo a treatment plan for curing or managing progression or symptoms of the disease. These treatment plans commonly include surgery, radiation therapy, chemotherapy, hormone therapy, immunotherapy or a combination of these therapies. While the aim of these therapies is to kill cancer cells, some healthy cells can also become damaged and killed in the treatment process. The death of healthy cells can cause various side effects such as loss of appetite, weight loss or gain, nausea and vomiting. These side effects can significantly hinder the cancer patient's ability to eat and assimilate necessary nutrients. The present invention provides a means of reducing the damage to, and restoring, healthy cells through the specific provision of nutrients by means of the vegetable juice therapy.

Additionally, arthritis patients suffer from inflammation of the joints. The present invention helps alleviate the inflammation and mitigate the side effects of biologic and immuno-therapies for arthritis.

The present invention comprises a therapy that is based on a specific vegetable juice formulation and cleansing application designed to meet the nutritional needs of patients undergoing cancer treatment by traditional means such as surgery, radiation therapy, chemotherapy, hormone therapy, immuno therapy, as well as to supplement such treatment by arming the patient with the relevant nutritional weapons to support general health in a safe and simple manner.

The aforementioned therapy consists of:
i. Cleansing application
and
ii. Vegetable juice therapy While the therapy is to be supplemented by proper dieting and exercise and meditation, the cleansing application and vegetable juice therapy are the aspects of the present invention.

The cleansing application is designed to purify the body and rid same of any waste matter, so as to allow other aspects of the treatment to take their full effect. The cleansing application should be administered first thing in the morning during treatment, for the full duration, and comprises one or more and preferably all of the following:
i. about 2 fluid ounces (59.1 ml) of lemon juice diluted up to 50% by volume with approximately body-temperature water (4 fluid ounces if fully diluted);
ii. about 1.5-2 fluid ounces (44.3-59.1 ml) of lime juice diluted up to 50% by volume with approximately body-temperature water (3-4 fluid ounces if fully diluted);
iii. about 1 fluid ounce (59.1 ml) of blended *Aloe Vera* diluted up to 50% by volume with approximately body-temperature water (2 fluid ounces if fully diluted);
iv. about 4-6 fluid (118.3 to 177.4 ml) of Cranberry juice Because tap water can contain chemicals, distilled or other purified water is preferred for purposes of dilution.

The vegetable juice therapy is designed to provide the right balance of nutrients to promote cell regeneration and growth and promote general health. The vegetable juice therapy also contains very powerful cleansing agents which manifest themselves during treatment. The vegetable juice therapy comprises a combination of the following, in raw form, prior to extraction:
i. about 8-10 ounces by weight (226.8 to 283.5 g) carrots (excluding greens)
ii. about 4-5 ounces by weight (113.4 to 141.8 g) beetroot (excluding greens)
iii. about 4-5 ounces by weight (113.4 to 141.8 g) cucumber
iv. about 1-2 tsp. (3.5 to 10 ml) of blended liquid *aloe vera*

Thus, the vegetable therapy constitutes a liquid extracted from equal parts, by weight, raw, unpeeled beetroot and cucumber, and about twice the amount (two parts) of carrots, by weight, with the addition of a relatively small quantity of *aloe vera* juice.

As mentioned herein, addition of ingredients with high sugar content should be avoided. Further, to avoid oxidation of the ingredients prior to ingestion and absorbtion, addition of fruits, especially citrus, and acidic vegetables, such as tomatoes, should be avoided.

Mode of Use for Vegetable Therapy

In order for the therapy to have maximum effect the following directions must be observed:
1. Use fresh unpeeled vegetables.
2. Scrub and wash vegetables properly.
3. Cut vegetables into suitable sizes (the sizes may vary depending on the juice extractor used).
4. Place vegetables into juice extractor and process
5. Add 5-10 ml. of the liquid *Aloe Vera* (see below for preparation of *Aloe Vera*) to the extracted juice.
6. Drink immediately.
7. Take twice daily.

It is essential that a juice extractor rather than a blender be used as a blender does not produce the level of concentration that is required. Use of a blender also causes extra exposure of the juice which can lead to oxidation and the consequent destruction of vital elements of the vegetables. By extractor is meant a device that relies primarily if not exclusively on application of pressure to the fruits and vegetables to obtain juice, rather than maceration, cutting, or grinding. As mentioned, such maceration exposes the fruits and vegetables and resulting juice to excessive oxidation, reducing the effectiveness of the treatment. Exposure of the cut fruits and vegetables to air can also lead to oxidation. Accordingly, both the cut vegetables and the extracted juices should be minimally exposed to air before consumption to maximize effectiveness.

Further to steps 4 and 5 above, the extract of all three vegetables should be combined and then the liquid *aloe vera* (see below) added to same. Further to step 6 above, the vegetable extract must be consumed immediately after extraction to prevent the destruction of micro-elements by oxidation and exposure to oxygen and oxidative materials, such as acids from citrus and other fruits and vegetables should be minimized. Further to step 6 above, the vegetable juice therapy, which should ultimately consist of 6-8 ozs of juice, should be taken twice daily. In the instance where the patient has recovered, the vegetable therapy should be continued once daily as a preventative measure.

While the above-mentioned therapy can be taken first thing in the morning, it is a flexible therapy in terms of time of day that it may be taken and it can also be administered either before or after meals. As the user's stomach is usually empty first thing in the morning, there is an added benefit of taking the therapy at that time in that it will have a more stimulating effect.

If the cancer affects the throat and particularly where radiation is being administered, the juice extract must be further filtered, by means of a filter cloth to eliminate all traces of sediments. Otherwise, remaining particles could cause extreme pain to the cancer patient when swallowed.

Steps for Preparation of *Aloe Vera*

The *Aloe Vera* represents a very powerful healing substance and should be prepared separately in the following manner:
1. Wash and cut the fresh, green *Aloe Vera* (do not use if a colour change has begun) into small pieces without trimming or removing the green portions or any part of the skin.
2. Add 225 grams of *Aloe* to approximately 500 ml. of water.
3. Blend and strain the combination and then cover it in an airtight container.
4. Store the container in a refrigerator, for not more than eight (8) days, until ready for use.
5. Add 5-10 ml of the blended *Aloe* to the juice extract prior to drinking.

The effectiveness of the vegetable juice therapy further requires that it should be kept covered at all times and not be combined with any other substance (including water) containing citrus, as the citrus will destroy the delicate elements in the vegetable juice. At no point should the therapy or any other aspect of the invention be used in conjunction with any form of herbal therapy, such as the Brandt Grape Cure therapy, as this might counteract the effectiveness of the invention.

The above-mentioned therapy and cleansing application is supplemented by adherence to proper diet and exercise.

The primary object of the invention is to promote general health and to significantly increase the prospects of full and rapid recovery of cancer patients who are also undergoing radiation therapy or chemotherapy, as well as arthritis patients, especially those undergoing treatment with biologics or immunotherapies.

The invention does not require a rigorous or painful application but can be administered by means of a simple and effective oral procedure.

As mentioned above, other treatments lead to certain side effects such as nausea or vomiting. The present invention assists in counteracting such side effects and also provides no side effects of its own.

It is known that certain treatments such as radiation and chemotherapy cannot, on their own, always provide for the successful recovery of a cancer patient. The present invention is a supportive treatment that ensures the rapid recovery of the patient.

The present invention is not chemically based and thus will not expose the user to any health risks.

The invention also provides a cost-effective means of accessing its benefits/uses.

I claim:
1. A dietary supplement for treatment of a patient undergoing cancer or arthritis treatment, the supplement consisting essentially of:
    juice extracted from about 4-5 ounces by weight (113.4 to 141.8 g) of fresh, unpeeled beet root;
    juice extracted from about 8-10 ounces by weight (226.8 to 283.5 g) of fresh, unpeeled carrots;
    juice extracted from a quantity of fresh unpeeled cucumber about equal to the quantity, by weight, of fresh, unpeeled beet root;
    about 1 teaspoon (5 to 10 ml) of *aloe vera* juice in a mixture with the extracted juices.
2. The dietary supplement of claim 1, further comprising a cleansing component comprising at least one of the following:
    about 2 fluid ounces (59.1 ml) of lemon juice;
    about 1.5 to 2 fluid ounces (44.3 to 59.1 ml) of lime juice;
    about 1 fluid ounce (29.6 ml) of *aloe vera* juice; and
    about 4-6 fluid ounces (118.3 to 177.4 ml) of cranberry juice.
3. The dietary supplement of claim 1, wherein the *aloe vera* juice comprises:
    about 8 ounces (225 grams) washed and cut, untrimmed, fresh, green *aloe vera* plant with intact skin;
    the *aloe vera* blended with about 16 fluid ounces (500 ml) of water and strained.
4. The dietary supplement of claim 1, wherein the mixture comprises 6 to 8 fluid ounces (177.4 to 236.6 ml).
5. A dietary supplement for a patient undergoing cancer or arthritis treatment, the supplement comprising:
    a vegetable component consisting essentially of juices extracted from:
        about 8-10 ounces by weight (226.8 to 283.6 g) fresh, unpeeled carrots;
        about 4-5 ounces by weight (113.4 to 141.8 g) fresh, unpeeled beet root;
        about 4-5 ounces by weight (113.4 to 141.8 g) fresh, unpeeled cucumber; and
    a selected quantity of *aloe vera* juice; and
    a cleansing component including at least one of the following:
        about 2 fluid ounces (59.1 ml) of lemon juice;
        about 1.5-2 fluid ounces (44.3 to 59.1 ml) of lime juice;
        about 1 fluid ounce (29.6 ml) of *aloe vera* juice; and
        about 4-6 fluid ounces (118.3 to 177.4 ml) of cranberry juice.
6. The dietary supplement of claim 5, wherein the selected quantity of *aloe vera* juice is 1 teaspoon (5 to 10 ml).
7. The dietary supplement of claim 5, wherein the vegetable component comprises of about 6 to 8 fluid ounces (177.4 to 236.6 ml) of the vegetable juice.
8. The dietary supplement of claim 5, wherein the *aloe vera* juice comprises:
    about 225 grams (8 ounces) washed and cut, untrimmed, fresh, green *aloe vera* plant with intact skin, the *aloe vera* blended with about 500 ml (16 fluid ounces) of water and strained.
9. A method of a dietary supplementation for a patient undergoing cancer or arthritis treatment, the method consisting essentially of the steps of:
    extracting juice from about 8-10 ounces by weight (226.8 to 283.5g) fresh, unpeeled carrots;
    extracting juice from about 4-5 ounces by weight (113.4 to 141.8g) fresh, unpeeled beet root;
    extracting juice from about 4-5 ounces by weight (113.4 to 141.8g) fresh, unpeeled cucumber;

mixing the extracted carrot, beet root, and cucumber juices with a selected quantity of *aloe vera* juice and administering the mixture to the patient twice daily; and orally administering to the patient once daily at least one of the following:

about 2 fluid ounces (59.1 ml) of lemon juice;
about 1.5-2 fluid ounces (44.3 to 599.1 ml) of lime juice;
about 1 fluid ounce (29.6 ml) of *aloe vera* juice; and
about 4-6 fluid ounces (118.3 to 177.4 ml) of cranberry juice.

10. The method of claim 9, wherein the *aloe vera* juice is prepared by a method comprising the steps of:

washing fresh, green *aloe vera* plant before any color change;
cutting the washed *aloe vera* plant into pieces without trimming or removing green portions or any skin;
blending the washed and cut *aloe vera* pieces with water; and
straining the blended *aloe vera* and water.

11. The method of claim 10, wherein the proportion of *aloe vera* to water is about 4.5:10.

12. The method of claim 9, wherein 6 to 8 fluid ounces (177.4 to 236.6 ml) of the mixture is administered.

\* \* \* \* \*